(12) United States Patent
Oe (10) Patent No.: US 9,757,026 B2
(45) Date of Patent: Sep. 12, 2017

(54) OPHTHALMIC APPARATUS (71) Applicant: Kabushiki Kaisha TOPCON, Tokyo-to (JP)

(72) Inventor: Hiroki Oe, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 0 days.

(21) Appl. No.: 14/896,498

(22) PCT Filed: Jun. 5, 2014

(86) PCT No.: PCT/JP2014/065525
§ 371 (c)(1),
(2) Date: Dec. 7, 2015

(87) PCT Pub. No.: WO2014/200042
PCT Pub. Date: Dec. 18, 2014

(65) Prior Publication Data
US 2016/0128564 A1 May 12, 2016

(30) Foreign Application Priority Data

Jun. 11, 2013 (JP) ................. 2013-122689

(51) Int. Cl.
*A61B 3/14* (2006.01)
*A61B 3/10* (2006.01)
(Continued)

(52) U.S. Cl.
CPC .......... *A61B 3/1005* (2013.01); *A61B 3/0025* (2013.01); *A61B 3/0033* (2013.01);
(Continued)

(58) Field of Classification Search
CPC ........... A61B 3/152; A61B 3/14; A61B 3/103; A61B 3/113; A61B 3/1208; A61B 3/1225; A61B 3/024; A61B 3/032; A61B 3/1015
(Continued)

(56) References Cited

U.S. PATENT DOCUMENTS

| 5,548,354 A * | 8/1996 | Kasahara | A61B 3/0058 351/206 |
| 2013/0278898 A1* | 10/2013 | Kato | A61B 3/1005 351/208 |
| 2013/0286350 A1* | 10/2013 | Sakashita | A61B 3/14 351/208 |

FOREIGN PATENT DOCUMENTS

| JP | 6-269413 A | 9/1994 |
| JP | 2007-130246 A | 5/2007 |

(Continued)

OTHER PUBLICATIONS

International Preliminary Report on Patentability mailed Dec. 23, 2015 in corresponding PCT application No. PCT/JP2014/065525.

*Primary Examiner* — Dawayne A Pinkney
(74) *Attorney, Agent, or Firm* — Nields, Lemack & Frame, LLC (57) ABSTRACT

An ophthalmic apparatus which photographs an endothelial cell and measures a coat thickness of a cornea of an eye to be examined in a non-contact manner; comprising an image pickup unit (19) for photographing a corneal endothelium of the eye to be examined, a control unit (49) for detecting a cell wall of the endothelial cell from a corneal endothelial image photographed by the image pickup unit and for performing an image processing of hatching the cell wall with a boundary line, a display unit (54) for displaying an analytical image in which the cell wall hatched with the boundary line, and an operation unit (55), wherein the (Continued)

control unit changes the shading of the boundary line based on an input from the operation unit.

2 Claims, 5 Drawing Sheets

(51) Int. Cl.
*A61B 3/00* (2006.01)
*A61B 3/107* (2006.01)
*A61B 3/15* (2006.01)

(52) U.S. Cl.
CPC ............ *A61B 3/0058* (2013.01); *A61B 3/107* (2013.01); *A61B 3/14* (2013.01); *A61B 3/152* (2013.01)

(58) Field of Classification Search
USPC ........ 351/208, 206, 200, 205, 209–211, 218, 351/221–223, 246
See application file for complete search history.

(56) References Cited

FOREIGN PATENT DOCUMENTS

JP 2008036303 A * 2/2008
JP 2011-224128 A 11/2011

* cited by examiner

OPHTHALMIC APPARATUS

TECHNICAL FIELD

The present invention relates to an ophthalmic apparatus for diagnosing soundness of cornea which photographs endothelial cells of a cornea.

BACKGROUND ART

In an ophthalmic apparatus which measures a corneal endothelium, by photographing a corneal endothelial image and analyzing the corneal endothelial image a corneal endothelium is measured, and a shape, a size, or the like of the endothelial cell are detected.

The corneal endothelium is made of endothelial cells which cannot be regenerated, and the soundness of the endothelial cell is diagnosed based on size and shape of the endothelial cell. Further, the size of the endothelial cell can be determined, based on a density of the endothelial cell, and the shape can be determined based on a fluctuation in area of the endothelial cell. With respect to the density of the endothelial cells, by counting the number of the endothelial cells in an image photographed, the density of the endothelial cell can be obtained as a statistic based on a photographed range and the number.

From a corneal endothelial image photographed, a cell wall of the endothelial cells, for determining a shape or a size of the endothelial cell, can be obtained by analyzing a boundary line as hatched. However a position of the boundary line does not necessarily coincide with a position of each cell wall, and when the analysis is performed, an examiner needs to display a corneal endothelial image on a monitor or the like, to judge whether positions of the cell wall and the boundary line coincide with each other from the displayed corneal endothelial image, and to execute an edit processing, for instance, an addition or a deletion of the boundary line as required.

However, since a conventional ophthalmic apparatus only has a function of turning on/off the boundary line in the corneal endothelial image, the boundary line is hard to be seen depending on the brightness of the corneal endothelial image in some cases, and it is difficult to judge whether the position of the cell wall and the boundary line coincide with each other.

PRIOR ART REFERENCES

Patent Document

Patent Document 1: Patent Publication JP-A-2007-130246

SUMMARY OF THE INVENTION

Problem to be Solved by the Invention

To solve the problems as described above, it is an object of the present invention to provide an ophthalmic apparatus which can easily discriminate a cell wall of an endothelial cell from a boundary line irrespective of brightness and darkness of a corneal endothelial image.

Means for Solving the Problem

The present invention relates to an ophthalmic apparatus which photographs an endothelial cell and measures a coat thickness of a cornea of an eye to be examined in a non-contact manner; comprising an image pickup unit for photographing a corneal endothelium of the eye to be examined, a control unit for detecting a cell wall of the endothelial cell from a corneal endothelial image photographed by the image pickup unit and for performing an image processing of hatching the cell wall with a boundary line, a display unit for displaying an analytical image in which the cell wall hatched with the boundary line, and an operation unit, wherein the control unit changes the shading of the boundary line based on an input from the operation unit.

Further, the present invention relates to the ophthalmic apparatus, wherein the display unit also serves as a touch panel as the operation unit, and the control unit detects a pressing of a screen with respect to the display unit and changes shading of the boundary line based on a sliding direction and a distance from a pressed position.

Furthermore, the present invention relates to the ophthalmic apparatus, wherein the control unit aligns and displays the corneal endothelial image and the analytical image on the display unit.

Effects of the Invention

According to the present invention, an ophthalmic apparatus which photographs an endothelial cell and measures a coat thickness of a cornea of an eye to be examined in a non-contact manner; comprising an image pickup unit for photographing a corneal endothelium of the eye to be examined, a control unit for detecting a cell wall of the endothelial cell from a corneal endothelial image photographed by the image pickup unit and for performing an image processing of hatching the cell wall with a boundary line, a display unit for displaying an analytical image in which the cell wall hatched with the boundary line, and an operation unit, wherein the control unit changes the shading of the boundary line based on an input from the operation unit. As a result, even in a portion which is hard to be determined by simply turning on/off the boundary line according to the brightness and darkness of the corneal endothelial image, it is possible to easily determine whether a position of the cell wall and a position of the boundary line coincide with each other, and also possible to improve the workability and the accuracy of operations.

Further, according to the present invention, the display unit also serves as a touch panel as the operation unit, and the control unit detects a pressing of a screen with respect to the display unit and changes shading of the boundary line based on a sliding direction and a distance from a pressed position. As a result, it is possible to improve an operability, and to further improve the workability and the accuracy of operations.

Furthermore, according to the present invention, the control unit aligns and displays the corneal endothelial image and the analytical image on the display unit. As a result, it is possible to easily determine whether a position of the cell wall coincides with a position of the boundary line and to improve the workability.

BRIEF DESCRIPTION OF DRAWINGS

FIG. 6 is explanatory drawings showing a display example of a manual edit screen displayed in the display unit of the ophthalmic apparatus, in which

MODE(S) FOR CARRYING OUT THE INVENTION

A description will be given below on embodiments of the present invention by referring to the attached drawings.

First, a description will be given on a schematic configuration of an ophthalmic apparatus according to an embodiment of the present invention by referring to FIG. 1 to FIG. 3.

Figure 1:
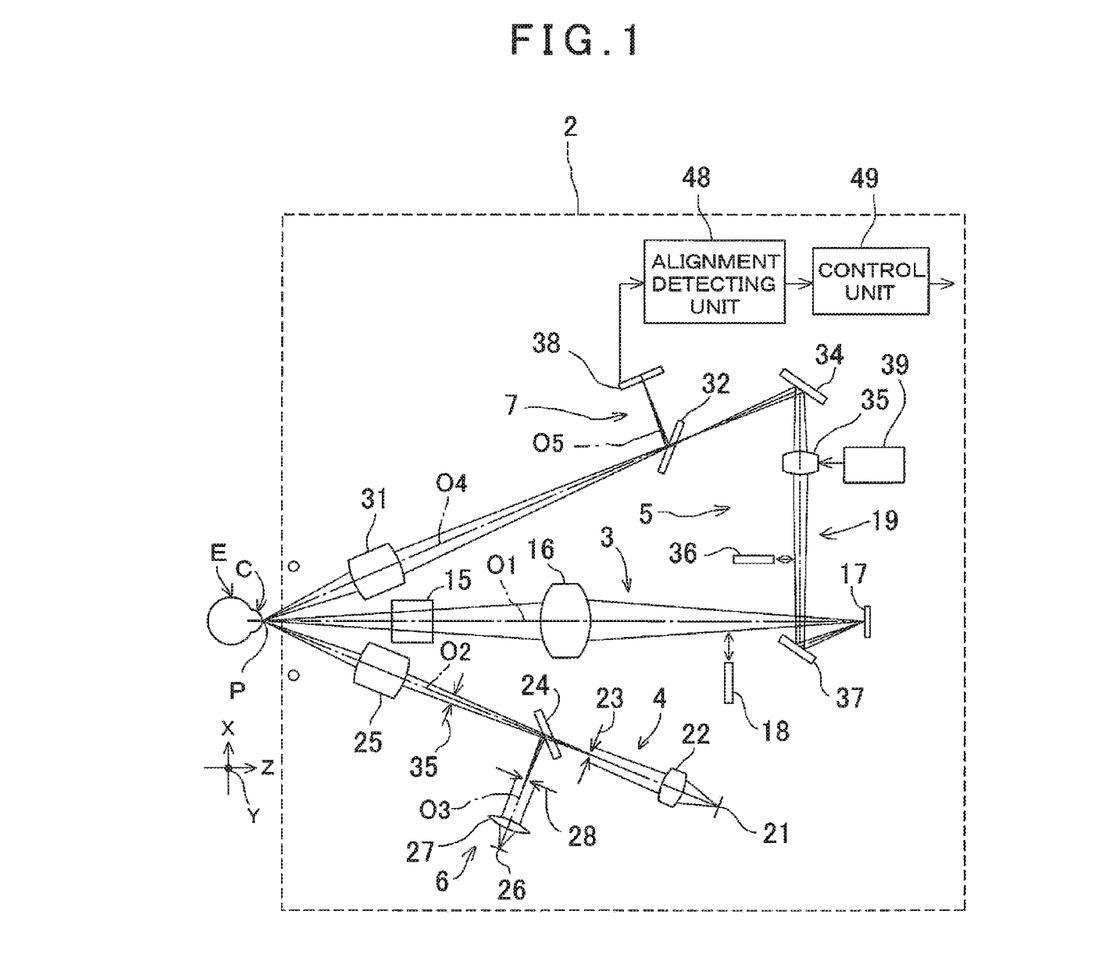
FIG. 1 is a schematic block diagram of an ophthalmic apparatus according to an embodiment of the present invention.

In FIG. 1, a reference symbol E denotes an eye to be examined, and a reference numeral 2 denotes an apparatus main body which can move in three axial directions of X, Y, and Z. The apparatus main body 2 has an anterior ocular segment observation optical system 3, an illumination optical system for photographing 4, a photographing optical system 5, a Z alignment projection system 6, and a Z alignment detection system 7 therein.

Figure 2:
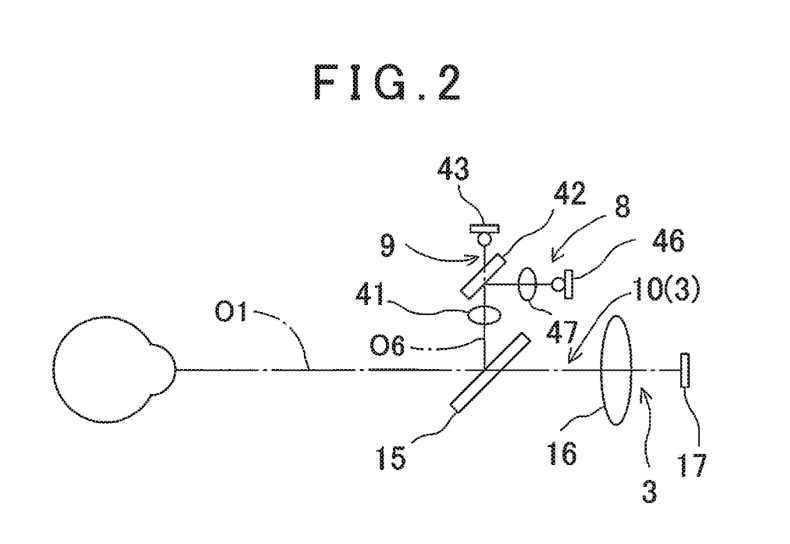
FIG. 2 is a schematic block diagram showing an XY alignment projection system and a fixation projection system in the ophthalmic apparatus.

Further, as shown in FIG. 2, the apparatus main body 2 has an XY alignment projection system 8 and a fixation projection system 9 provided therein, and an XY alignment detection system 10 doubles as the anterior ocular segment observation optical system 3.

A configuration will be further described.

In FIG. 1, the anterior ocular segment observation optical systems 3 are arranged in accordance with the left and right eyes to be examined E, a main optical axis O1 of the anterior ocular segment observation optical system 3 is provided so as to coincide with an optical axis of each eye to be examined E, and the main optical axis O1 is set to pass through an apex P of a cornea of the eye to be examined E.

A half mirror 15, an objective lens 16, a photodetection element 17 are provided on the main optical axis O1 from a side close to the eye to be examined E, and a light shielding plate 18, which can be inserted into or removed from the main optical axis O1, is provided. A CCD element is used as the photodetection element 17, and the photodetection element 17 is arranged at a position conjugate to a cornea C of the eye to be examined P with respect to the objective lens 16. The photographing optical system 5 and the photodetection element 17 or the like, constitute an image pickup unit 19.

The light shielding plate 18 is retreated from the main optical axis O1 when observing an anterior ocular segment, and inserted into an optical path when photographing a corneal endothelial cell as described later.

The illumination optical system for photographing 4 has a projection optical axis O2 which is inclined at a predetermined angle, for instance, any angle from 17° to 22° with respect to the main optical axis O1 and passes through the apex P. An illumination light source for photographing 21, a condenser lens 22, a slit plate 23, a dichroic mirror 24, and an objective lens 25 are provided on the projection optical axis O2 from a position distant from the eye to be examined E.

As the illumination light source for photographing 21, a light-emitting diode (LED) which emits a visible light, for instance, a green light is used. A slit hole is formed in the slit plate 23, and a visible light emitted from the illumination light source for photographing 21 is irradiated as a slight light. Further, a slit width formed by the slit plate 23 is restricted to a width which enables separating a reflection light reflected on a surface of the cornea C from a reflection light from an endothelium.

The Z alignment projection system 6 has a light source 26, a condenser lens 27, and a slit plate 28 arranged on an optical axis O3 branched by the dichroic mirror 24. As the light source 26, a light-emitting diode (LED) which emits an infrared light is used.

The dichroic mirror 24 is adapted to transmit the green light therethrough and reflects the infrared light. Further, the slit plate 23, the slit plate 28, and the cornea C are conjugate with respect to the objective lens 25.

The photographing optical system 5 has a photographing optical axis O4 which is symmetrical to the projection optical axis O2 with respect to the main optical axis O1, and the photographing optical axis O4 passes through the apex P.

On the photographing optical axis O4, an objective lens 31, a dichroic mirror 32, and a mirror 34 are provided from the side close to the eye to be examined E. The photographing optical axis O4 is deflected by the mirror 34, a relay lens 35 for adjusting focus and a mirror 37 are provided on the photographing optical axis O4, and a luminous flux reflected by the mirror 37 is focused on the photodetection element 17. A shielding plate 36 can be inserted into or removed from the photographing optical axis O4 passing through the relay lens 35. Further, the dichroic mirror 32 has transmission characteristics of transmitting a visible light and reflecting an infrared light. The relay lens 35 can be moved in an optical axis direction by a lens drive mechanism 39.

A photodetection sensor 38 is provided on an optical axis O5 reflected and deflected by the dichroic mirror 32, and the photodetection sensor 38 and the cornea C are conjugate with respect to the objective lens 31. The dichroic mirror 32 has the optical characteristics of reflecting the infrared light and transmitting the green light therethrough, and leads the infrared light emitted from the light source 26 and reflected by the cornea C to the photodetection sensor 38. The dichroic mirror 32 and the photodetection sensor 38 constitute the Z alignment detection system 7.

A relay lens 41 and a dichroic mirror 42 are provided on an optical axis O6 branched by the half mirror 15, and further a fixation light source 43 is provided on an optical axis passing through the dichroic mirror 42.

Figure 3:
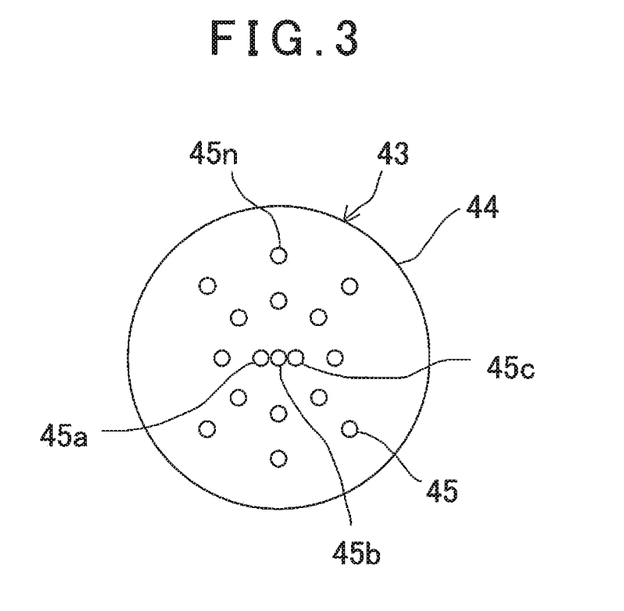
FIG. 3 is an explanatory drawing of a fixation light source which is an example of a fixation target used in the fixation projection system.

As shown in FIG. 3, the fixation light source 43 has a plurality of light-emitting diodes (LEDs) 45 provided on a light-emitting element holding plate 44. Two or three of the LEDs 45 (three in the drawing, i.e. 45a, 45b and 45c) are arranged along a width direction of a slit light around a position as their center where the optical axis O6 passes. Further other some of the LEDs 45 are arranged on a circumference at a predetermined angle pitch around the position as their center where the optical axis O6 passes. The drawing shows an example where the three LEDs 45 are arranged in the slit width direction, and the eight and six LEDs 45 are arranged on the two concentric circles. The plurality of LEDs 45 emit the visible lights, for instance, the green light, and can be individually turned on.

It is to be noted that a pitch of the LEDs 45*a*, 45*b* and 45*c* provided in the width direction is set so that, in a case where a subject person fixates the LEDs 45*a*, 45*b* and 45*c*, the corneal endothelial images acquired through the photographing optical system 5 by the photodetection element 17 (the image pickup unit 19) can overlap in a necessary range.

On an optical axis reflected by the dichroic mirror 42, a relay lens 47 and a light source for XY alignment 46 are provided. As the light source for XY alignment 46, a light-emitting diode which emits an infrared light is used. The relay lens 47, the light source for XY alignment 46 or the like constitute the XY alignment projection system 8.

A result as photodetected by the photodetection sensor 38 and a result as photodetected by the photodetection element 17 are detected by an alignment detecting unit 48, and the detection results are output to a control unit 49. The control unit 49 controls a main body driving unit 52 (see FIG. 4) based on the detection results, moves the apparatus main body 2 in the directions as required of XYZ, and the alignment of the eye to be examined E and the apparatus main body 2 is executed.

Figure 4:
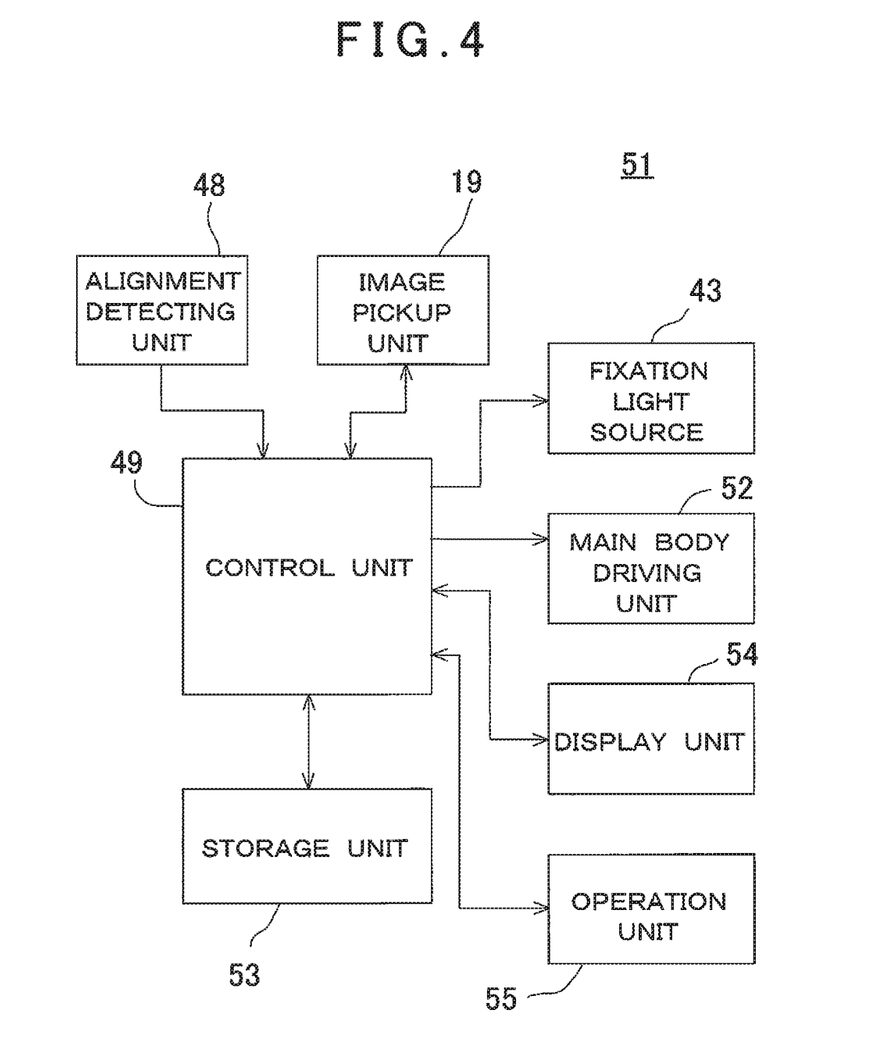
FIG. 4 is a schematic block diagram of a control device of the ophthalmic apparatus.

FIG. 4 shows general features of a control device 51 of the ophthalmic apparatus.

The control device 51 mainly comprises the image pickup unit 19, the alignment detecting unit 48, the fixation light source 43, the main body driving unit 52, a storage unit 53, an operation unit 55, and a display unit 54. It is to be noted that, in this embodiment, the display unit 54 is a touch panel which also serves as an operation unit so that the various kinds of operations can be executed through the display unit 54.

When an alignment detection result is input from the alignment detecting unit 48, the control unit 49 drives the main body driving unit 52 based on the detection result, and displaces the apparatus main body 2 in a direction to align. Further, the control unit 49 synchronously controls the image pickup unit 19 and the fixation light source 43, controls the lighting of the individual LEDs 45*a*, 45*b* and 45*c*, and also acquires an image of an endothelial cell (a corneal endothelial image) by the image pickup unit 19.

Further, the corneal endothelial image 59 (to be described later) acquired by the image pickup unit 19 is sent to the control unit 49, and a predetermined analysis processing, for instance, the detection of cell walls of endothelial cells, an arithmetic operation of the number and density of the endothelial cells, an arithmetic operation of a corneal thickness, or the like is executed. Then, an image processing as required is performed with respect to the corneal endothelial image 59 based on an analysis result, and is stored in the storage unit 53 or displayed on the display unit 54.

Figure 5:
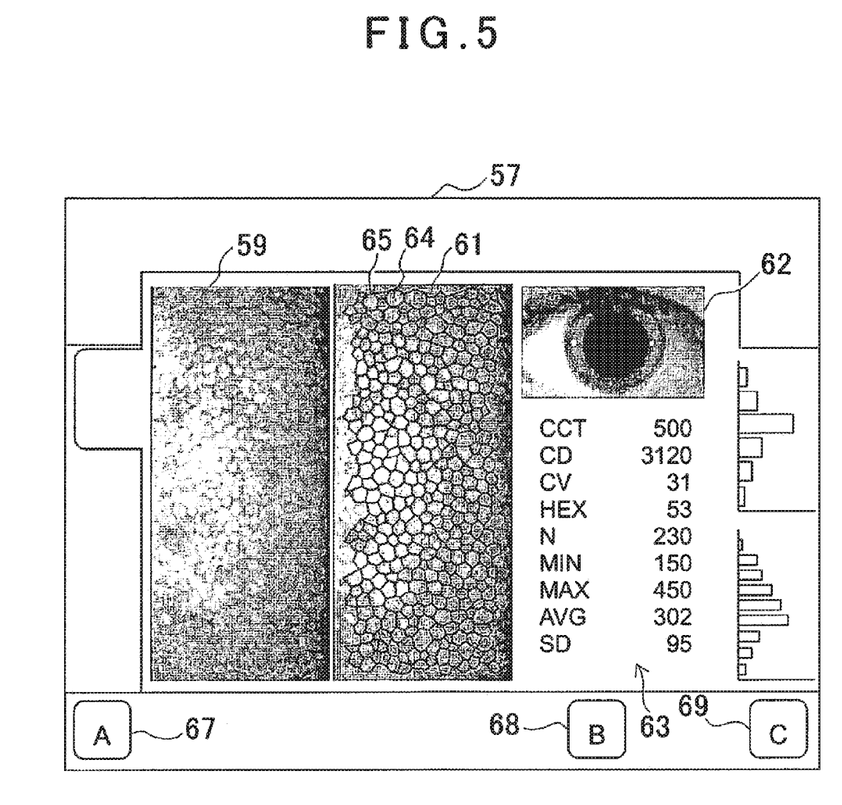
FIG. 5 is an explanatory drawing showing a display example of an analysis result screen displayed in a display unit of the ophthalmic apparatus.

FIG. 5 shows an analysis result screen 57 displayed on the display unit 54 after photographing a corneal endothelium by the image pickup unit 19.

In a screen central portion of the analysis result screen 57, the corneal endothelial image 59 and an analytical image 61 are aligned and displayed, and an anterior ocular segment image 62 and the various analysis results 63 are displayed on right side of a screen of the analytical image 61.

The corneal endothelial image 59 is an original image of the corneal endothelium which is not performed the image processing, and the analytical image 61 is an image acquired by performing the image processing to the corneal endothelial image 59 and hatching a cell wall of detected endothelial cell 64 by a boundary line 65 of a predetermined color, for instance, a black color.

Further, as the analysis results 63, the analytical values, for instance, a corneal thickness (CCT), the cell density (CD), a coefficient of variation (CV), a hexagonal cell incidence rate (HEX), the number of analyzed cells (N), a minimum cell area (MIN), a maximum cell area (MAX), an average cell area (AVG), a cell area standard deviation (SD), or the like are displayed, and a graph indicating a distribution of shapes of the endothelial cells 64, a distribution of areas, or the like are displayed.

It is to be noted that, it is so arranged that in the analysis result screen 57, when the analytical image 61 is pressed by a finger or the like, the control unit 49 can detect a direction and a distance of sliding the finger, and change the shading (a degree of transparency) of the boundary line 65 based on the sliding direction and distance as detected.

For instance, in a case where the finger pressing the analytical image 61 is slid downward, the color of the boundary line 65 fades, and the boundary line 65 disappears and coincides with the corneal endothelial image 59 in the end. Further, in a case where the finger pressing the analytical image 61 is slid upward, the color of the boundary line 65 becomes thick, and in the end the boundary line 65 is displayed darkly and coincides with the analytical image 61 shown in FIG. 5.

Further, in a screen lower portion of the analysis result screen 57, the various instruction input buttons, for instance, a photographing retry button 67, a manual edit button 68, a next region button 69, or the like are displayed and, it is so arranged that by an examiner pressing an instruction input button by the finger or the like, an instruction corresponding to each instruction input button is input to the control unit 49.

Pressing the photographing retry button 67 enables the same region to be again photographed, pressing the manual edit button 68 enables the display of the display unit 54 to be switched to a manual edit screen 71 (to be described later). If there are two or more regions to be photographed, pressing the next region button 6 enables the next region to be photographed.

Figure 6A:
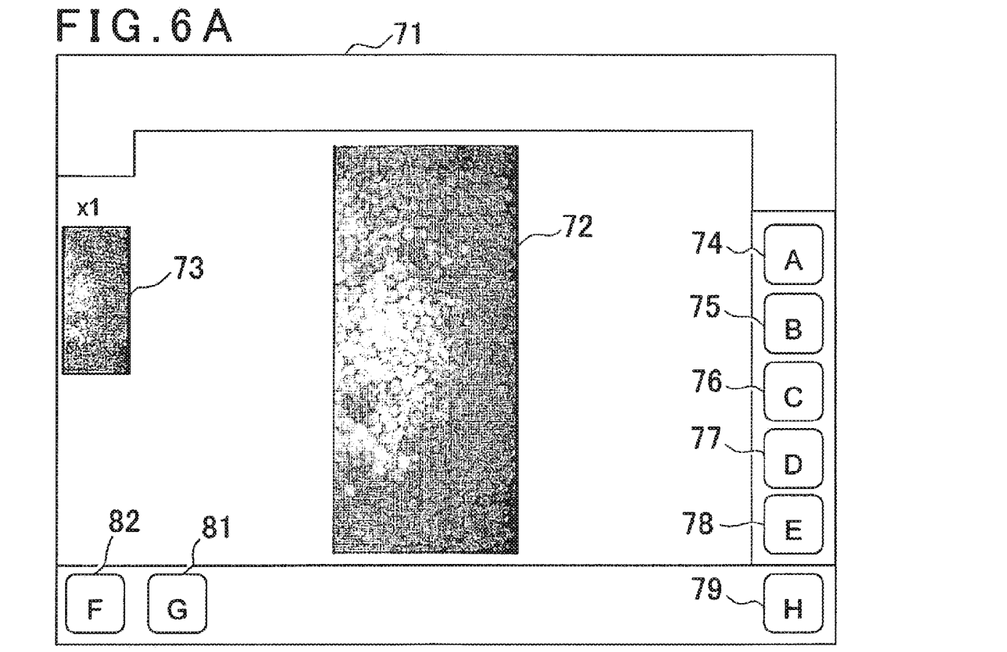
FIG. 6A shows a case where a shading of a boundary line is minimum and FIG. 6B shows a case where the shading of the boundary line is maximum.
Figure 6B:
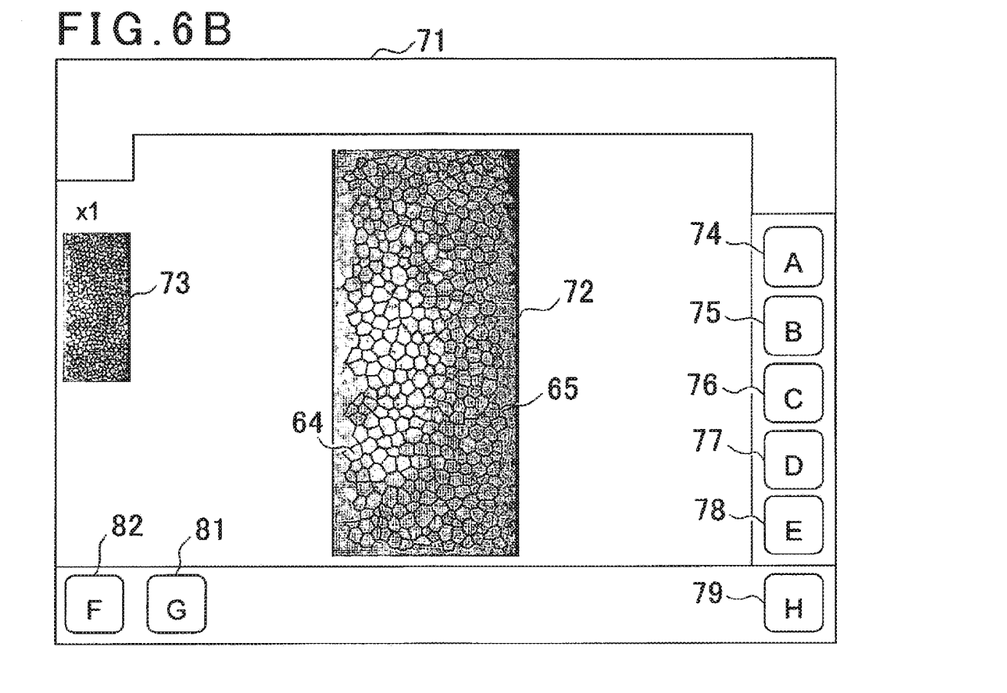

FIG. 6A and FIG. 6B represent the manual edit screens 71.

In the screen central portion of each manual edit screen 71 an edit image 72 is displayed, in a screen left end portion of the edit image 72 a thumbnail image 73 is displayed. Further, in a screen right end portion and a lower end portion of the manual edit screen 71 the various instruction input buttons, for instance, a boundary line addition button 74, a boundary line deletion button 75, an elimination button 76, an image processing button 77, a scaling button 78, a restoration button 79, an application button 81, a cancel button 82, and others are displayed and, when an examiner presses the instruction input button by the finger or the like, an instruction corresponding to each instruction input button is input to the control unit 49.

The thumbnail image 73 is an image which shows the entire of the analytical image 61 and the edit image 72 is a magnified image acquired by magnifying a designated part in the thumbnail image 73 at a designated magnification. It is to be noted that, in the drawing, since the designated magnification is one magnification, the thumbnail image 73 equals to the edit image 72.

In the manual edit screen 71, for instance, when an examiner presses a predetermined part in the thumbnail image 73, the designated position is changed, and an image displayed as the edit image 72 can be switched over.

Further, in a case where the edit image 72 is a magnified image of a part of the thumbnail image 73, by pressing the edit image 72 and by sliding a finger in an arbitrary direction while maintaining the pressed state, a display position of the edit image 72 can be shifted in accordance with the sliding direction and distance.

Further, it is so arranged that in the manual edit screen 71, like the analysis result screen 57, in a case where a part other than the edit image 72 and the thumbnail image 73 in the manual edit screen 71 is pressed by a finger, the control unit 49 can detect a direction and a distance of sliding the finger, and change shading of the boundary line 65 based on the detected sliding direction and distance.

For instance, in a case where the finger pressing the manual edit screen 71 is slid downward, as shown in FIG. 6A, the color of the boundary line 65 fades, and tin the end, the boundary line 65 disappears and coincides with the corneal endothelial image 59 displayed on the analysis result screen 57. Further, in a case where the finger pressing the manual edit screen 71 is slid upward, as shown in FIG. 6B, the color of the boundary line 65 becomes thick, and in the end, the boundary line 65 is displayed darkly and coincides with the analytical image 61 displayed on the analysis result screen 57.

When editing the edit image 72, pressing the boundary line addition button 74 enables switching over to a mode of adding the boundary line 65 in the edit image 72, and tracing a cell wall on the screen enables adding the boundary line 65 in a case where the boundary line 65 is not present at a position of the cell wall.

Further, pressing the boundary line deletion button 75 enables switching over to a mode of deleting the boundary line 65 in the edit image 72, and pressing the unnecessary boundary line 65 on the screen enables deleting the boundary line 65 in a case where the boundary line 65 is present at a position other than the cell wall.

Further, pressing the elimination button 76 enables switching over to a mode of eliminating the endothelial cell 64 in the edit image 72 surrounded by the boundary line 65 from the analysis, and pressing the endothelial cell 64 on the screen enables eliminating the pressed endothelial cell 64 from an analysis target.

Further, pressing the image processing button 77 allows the control unit 49 to execute the image processing, and to display an image emphasizing an edge in order to easily see the endothelial cell 64. Further, pressing the scaling button 78 enables changing a designated magnification of the edit image 72 and enables the edit image 72 to be magnified or minified.

Further, pressing the restoration button 79 enables discarding the edited contents in the manual edit screen 71 and restoring an original state. Pressing the application button 81 enables applying the edited contents in the manual edit screen 71 and returning to the analysis result screen 57. Further, pressing the cancel button 82 enables discarding the edited contents in the manual edit screen 71 and returning to the analysis result screen 57.

Thus, when an examiner presses each instruction input button displayed on the display unit 54, the conditions required for the photographing, an instruction, for instance, the start of photographing or the like, are input to the control unit 49, and an instruction, for instance, the editing of a displayed image, the execution of processing as required, or the like is input.

An operation of the ophthalmic apparatus will now be described hereinafter.

First, the light source 26 is turned on, a reflection light at the cornea C is received by the photodetection sensor 38, a deviation between a photodetecting position and a reference position on the photodetection sensor 38 is obtained, and the apparatus main body 2 is displaced in the Z direction so that the deviation becomes 0. It is to be noted that a detection light emitting from the Z alignment projection system 6 has a slit-like shape, and hence the photodetection sensor 38 may be a line sensor extending in a width direction of the slit light.

A point-like light is emitted from the light source for XY alignment 46 after the completion of the Z alignment or concurrently with the Z alignment and reflected by the cornea C, the reflection light is received by the photodetection element 17, and a deviation between the photodetecting position and the reference position on the photodetection element 17 is obtained. The apparatus main body 2 is displaced in the X direction or the Y direction so that the deviation becomes 0, and the alignment is executed.

After the completion of the alignment, the photography of the corneal endothelium is started.

The LEDs 45a, 45b and 45c positioned at the center of the fixation light source 43 are turned on one by one at the predetermined time intervals. Further, the illumination light source for photographing 21 is turned on in synchronization with the lighting of the LEDs 45a, 45b and 45c, and an illumination light which has turned to the slit light via the slit plate 23 is projected to the cornea C.

When one of the LEDs 45a, 45b and 45c, for instance, the LED 45a is turned on, a visual axis of a subject person is fixated on the LED 45a, and the endothelium is photographed in a state of the eye to be examined E at this moment. Further, when the LEDs 45b and 45c are individually turned on, a direction of the visual axis is changed, and the corneal endothelium in a different region can be photographed.

A photographic result is displayed on the display unit 54 as the analysis result screen 57.

An examiner compares the corneal endothelial image 59 and the analytical image 61 aligned and displayed on the analysis result screen 57, and slides the finger pressing the analytical image 61 upward or downward, adjusts the shading of the boundary line 65, and judges whether the corneal endothelial image 59 has been normally photographed and whether the cell wall of the endothelial cell 64 is correctly hatched with the boundary line 65.

When the examiner judges that the corneal endothelial image 59 has been normally photographed and the boundary line 65 is correctly hatched, the examiner presses the next region button 69, photographs a subsequent region and makes a judgment like as described above on the analysis result screen 57 of the subsequent region.

When the examiner judges that the corneal endothelial image 59 has not been normally photographed, the examiner presses the photographing retry button 67, photographs the same region, and again makes the judgment on the analysis result screen 57 displayed on the display unit 54.

Further, when the examiner judges that the corneal endothelial image 59 has been normally photographed but the boundary line 65 is not correctly hatched, the examiner presses the manual edit button 68. The display on the display unit 54 is switched over from the analysis result screen 57 to the manual edit screen 71, and the examiner executes the edit processing.

In the manual edit screen 71, the examiner presses the scaling button 78, changes a magnification of the edit image 72, presses a position as required in the thumbnail image 73, makes to display a rough position of a part to be confirmed as the edit image 72, slides the finger pressing the edit image 72, and make to display the part to be confirmed.

Further, the examiner presses a part other than the edit image 72 and the thumbnail image 73 in the manual edit screen 71, slides the pressing finger upward or downward, and changes the shading of the boundary line 65. Then the examiner judges whether a position of the cell wall of the endothelial cell 64 coincides with a position of the boundary line 65.

Based on a judgment as described above, the examiner presses each instruction input button, and executes a predetermined edit processing, for instance, the addition or deletion of the boundary line 65, or the like. After editing, the examiner presses the application button 81, restores the display on the display unit 54 to the analysis result screen 57 and terminates the edit processing.

Finally, by pressing the next region button 69 in the analysis result screen 57, photographing the corneal endothelium in this region is terminated.

As described above, in the present embodiment, it is so arranged that by pressing the analyrical image 61 by the finger or the like in the analysis result screen 57 and sliding the pressing finger upward or downward, the control unit 49 changes the shading of the boundary line 65 based on the sliding direction and distance. Further, in the manual edit screen 71, likewise, it is so arranged that by pressing a part other than the edit image 72 and the thumbnail image 73 by the finger or the like and sliding the pressing finger upward or downward, the control unit 49 changes the shading of the boundary line 65 based on the sliding direction and distance.

Therefore, even in a portion which is hard to determine the boundary line 65 based on the brightness and darkness of an image by simply turning on/off, it is possible to easily determine whether a position of the cell wall of the endothelial cell 64 coincides with a position of the boundary line 65, and the workability and the accuracy of the edit processing can be improved.

Further, in the analysis result screen 57, the corneal endothelial image 59 which is an original image of the corneal endothelium photographed by the image pickup unit 19 and the analytical image 61 provided by hatching the cell wall of the endothelial cell 64 in the corneal endothelial image 59 with the boundary line 65 are aligned and the displayed, the corneal endothelial image 59 and the analytical image 61 can be compared with each other in the same screen, and hence whether the position of the cell wall of the endothelial cell 64 coincides with the position of the boundary line 65 can be easily determined. As a result, the workability can be improved.

Further, in the present embodiment, since the touch panel is used as the display unit 54, the various instructions can be directly input from the screen, and the operability can be improved.

It is to be noted that, in the present embodiment, the touch panel is used as the display unit 54, but clicking operation may be performed on the screen by the operation unit 55, for instance, a mouse or the like, and by moving the operation unit 55 up or down in the clicked state, the shading of the boundary line 65 may be changed.

Further, a scroll bar may be provided in each of the analysis result screen 57 and the manual edit screen 71, and the scroll bar may be moved by the finger or the operation unit 55, the shading of the boundary line 65 can be changed.

LEGEND OF REFERENCE NUMERALS

2 Apparatus main body
19 Image pickup unit
49 Control unit
51 Control device
54 Display unit
55 Operation unit
57 Analysis result screen
59 Corneal endothelial image
61 Analytical image
64 Endothelial cell
65 Boundary line
71 Manual edit screen
72 Edit image
73 Thumbnail image

The invention claimed is:

1. An ophthalmic apparatus which photographs an endothelial cell and measures a corneal thickness of an eye to be examined in a non-contact manner; comprising an image pickup unit for photographing a corneal endothelium of said eye to be examined, a control unit for detecting a boundary of said endothelial cell from a corneal endothelial image photographed by said image pickup unit and for performing an image processing of highlighting said boundary with a boundary line, a display unit for displaying an analytical image in which said boundary line of said endothelial cell is highlighted, and an operation unit, wherein said control unit changes a degree of transparency of said boundary line of said analytical image based on an input from said operation unit, wherein said display unit also serves as a touch panel for said operation unit, and said control unit detects a pressing of a screen with respect to said display unit and changes a degree of transparency of said boundary line based on a sliding direction and a distance from a pressed position.

2. An ophthalmic apparatus according to claim 1, wherein said control unit aligns and displays said corneal endothelial image and said analytical image on said display unit.

* * * * *